(12) United States Patent
Stoffella

(10) Patent No.: US 6,689,136 B2
(45) Date of Patent: Feb. 10, 2004

(54) IMPLANT FOR FIXING TWO BONE FRAGMENTS TO EACH OTHER

(75) Inventor: Rudolf Stoffella, Mödling (AT)

(73) Assignee: Waldemar Link GmbH & Co., Hamburg (DE)

(*) Notice: Subject to any disclaimer, the term of this patent is extended or adjusted under 35 U.S.C. 154(b) by 44 days.

(21) Appl. No.: 10/224,822

(22) Filed: Aug. 21, 2002

(65) Prior Publication Data

US 2003/0040750 A1 Feb. 27, 2003

(30) Foreign Application Priority Data

Aug. 21, 2001 (EP) .......................................... 01120083

(51) Int. Cl.[7] .............................................. A61B 17/58
(52) U.S. Cl. .............................. 606/72; 606/73; 606/75
(58) Field of Search ............................... 606/60, 62, 67, 606/72, 73, 75

(56) References Cited

U.S. PATENT DOCUMENTS 5,976,141 A    11/1999    Haag et al.

FOREIGN PATENT DOCUMENTS

DE    297 09 289 U1    5/1997
GB    2 266 246 A      10/1993

*Primary Examiner*—David O. Reip
(74) *Attorney, Agent, or Firm*—Alix, Yale & Ristas, LLP

(57) ABSTRACT

The implant for fixing two bone fragments to each other comprises a clasp with two arms which are connected to each other at one of their ends and in this area form an eyelet with an opening for passage of a screw which can be screwed into one of the two bone fragments, and it is characterized in that it has a guide bushing for the screw, which guide bushing is inserted into the clasp eyelet and is secured thereon.

20 Claims, 4 Drawing Sheets

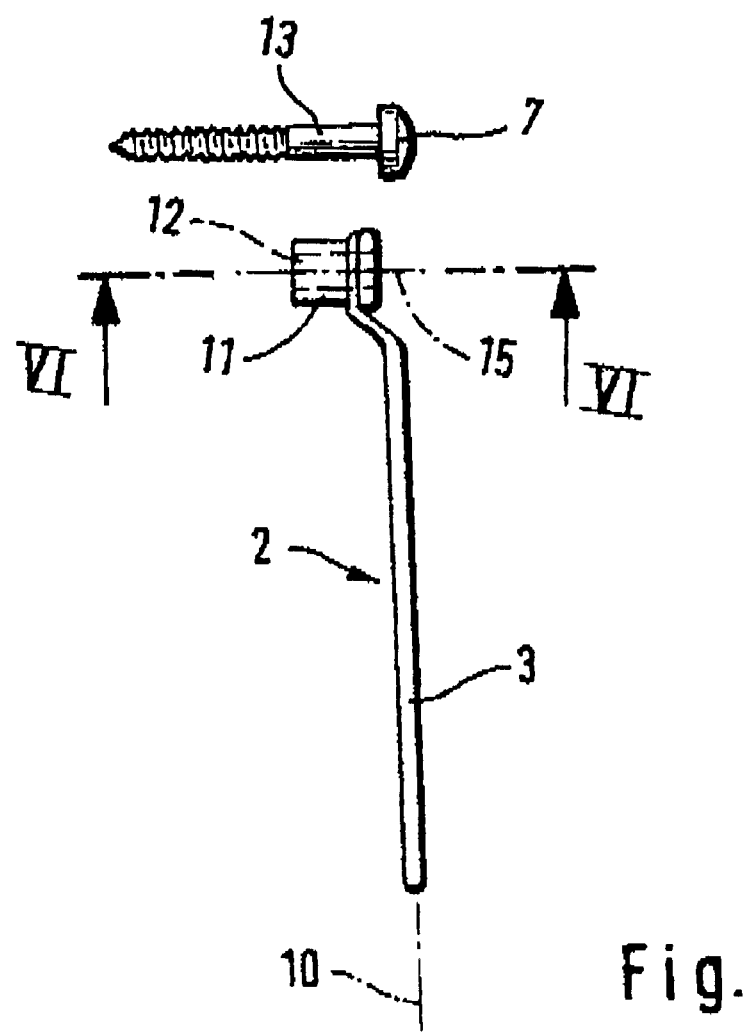

IMPLANT FOR FIXING TWO BONE FRAGMENTS TO EACH OTHER

BACKGROUND OF THE INVENTION

The invention relates to an implant for fixing two bone fragments to each other, in particular for fixing an axially corrected capitulum of a metatarsal bone, e.g. hallux valgus, which implant comprises a clasp with two arms which are connected to each other at one of their ends and in this area form an eyelet with an opening for passage of a screw which can be screwed into one of the two bone fragments, and which, with their other, free ends, can be introduced into the other bone fragment.

Osteotomies for treating hallux valgus have already been known for decades and have the object of functionally reconstructing the axis of the 1st metatarsal. It is necessary in this context, after the osteotomy, to fix the two bone fragments in their corrected position in order to prevent mobility between the fragments and to permit reliable osseous union without dislocation.

To fix the osteotomy, it is already known to use plates which are secured to the cortical bone by means of a number of screws in order to prevent the bone fragments from buckling. A considerable additional surgical effort is required for this.

Bone clamps are also known for fixing the osteotomy, but their use involves the risk of splintering of the bone.

AT 000 937 U has disclosed an implant for fixing two bone fragments to each other, in particular for treating an axial deviation of a metatarsal bone, e.g. hallux valgus, which implant comprises a clasp with two arms which are connected to each other at one of their ends and in this area delimit an opening for passage of a screw which can be screwed into one of the two bone fragments and which, with their other, free ends, can be introduced into the medullary cavity of the other bone fragment and can spread apart. After osteotomy has been performed, the clasp is introduced proximally into the medullary cavity of one bone fragment via the free ends of the two arms and spreads apart in this medullary cavity, after which the clasp is anchored on the other bone fragment by means of the screw guided through the opening.

As a result of the spreading force and the frictional fit of the clasp arms, and as a result of the intermittent compression arising upon functional loading, the intramedullary part of this known implant has a high degree of stability. By contrast, however, the extramedullary part is anchored in the bone via only one screw, whereas a two-point bearing is required on account of the torque which increasingly occurs as the compression of the screw anchoring between implant and metatarsal head decreases.

In order to improve and stabilize the fixing of this known implant to the bone fragment which is connected to the implant via the screw, it is known to provide, between the clasp opening and the screw head, a shim part through which the screw passes and which has projections which can be anchored in the bone fragment (WO 00/06036). Since this shim part is designed as a separate element, additional difficulties arise during implantation, and additional instruments are required.

The object of the invention is to make available an implant which is easier to implant and which, when implanted, ensures greater stability.

SUMMARY OF THE INVENTION

The solution according to the invention is for the implant to have a guide bushing for the screw, which guide bushing is inserted into the clasp eyelet and is secured thereon, its inner surface corresponding substantially to the outer surface of the screw in the area adjoining the screw head, and its minimum internal diameter being at least as great as the maximum diameter of the screw thread.

Thus, a shim part is no longer provided, but instead a guide bushing which is firmly secured on the clasp. In this way, implantation is easier, and no additional instruments are necessary. The invention, however, goes beyond this. Specifically, the guide bushing results in increased stability because the screw, in the implanted state, is fitted into said guide bushing in a manner substantially free of play, so that the angle stability between clasp and screw is ensured.

The inner surface of the guide bushing could, for example, have a slightly conical configuration, in which case the outer surface of the screw in the area adjoining the screw head is then of corresponding configuration so that the screw can be arranged substantially free of play in the guide bushing. In a particularly advantageous embodiment, however, the inner surface of the guide bushing and the corresponding outer surface of the screw are substantially cylindrical.

Another embodiment according to the invention is characterized by the fact that the inner surface of the guide bushing has a thread adapted to the outer surface of the screw.

In an advantageous embodiment, the guide bushing is secured on the clasp eyelet by having an edge area engaging at least partially around the clasp eyelet. In this case, it can be secured permanently on the clasp eyelet by turning the edge area back. The guide bushing can in this case have an annular recess at least partially receiving the clasp eyelet.

The surface with which the implant bears on the bone fragment connected to the implant via the screw must be offset in relation to the plane of the arms. In the prior art, this is achieved by the fact that the ends of the arms forming the clasp eyelet lie substantially in a plane which is parallel and offset in relation to the plane of the arms in which the remaining part of the arms lies. This can also be provided for in the implant according to the invention, but is not necessary, because the surface with which the implant bears on the bone fragment connected to the screw is laterally offset on account of the axial length of the guide sleeve when the guide sleeve extends axially from the clasp eyelet to the bearing surface. In any case, however, the bend of the area of the clasp eyelet can be made smaller, which has the advantage that the material here is not so strongly stressed upon bending and consequently there is much less risk of material breaks occurring in this area. However, the lateral offset of the clasp eyelet which can nevertheless be provided for has the advantage that in this case the screw does not project beyond the plane of the arms.

The inner surface of the guide bushing advantageously has a length of at least 3 mm in the axial direction.

BRIEF DESCRIPTION OF THE DRAWINGS

The invention is described below on the basis of advantageous embodiments and with reference to the attached drawings, in which:

FIG. 9 shows a further embodiment of the implant according to the invention.

DETAILED DESCRIPTION OF THE PREFERRED EMBODIMENT

Figure 1:
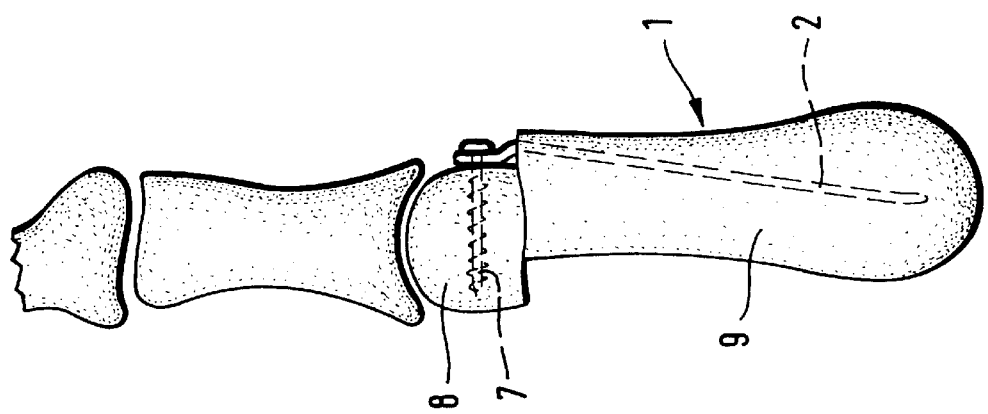
FIG. 1 shows the use of a previously known implant in the reconstruction of hallux valgus.

In FIG. 1, a metatarsal bone 1 is represented following osteotomy and repositioning. In the prior art, fixing is achieved using an implant which has a clasp 2 represented in FIGS. 1 to 3. This clasp has two arms 3 which are connected to each other at one of their ends at 4 and there delimit an opening 6 which is formed by an eyelet 5 and through which a screw 7 for small fragments (see FIG. 1) can be guided and anchored in the usual way in the bone fragment 8.

Figure 2:
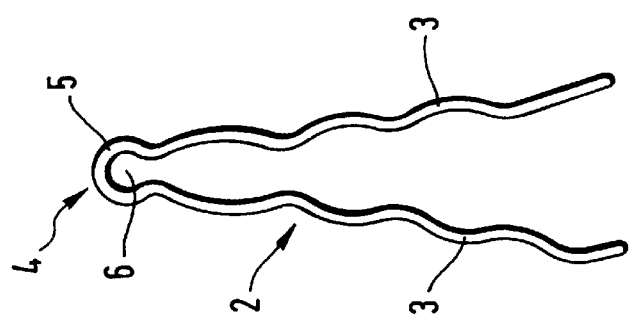
FIG. 2 shows the implant of the prior art in a plan view.

The two arms 3 of the clasp 2 are introduced into the medullary cavity of the bone fragment 9 and there take up their spread-apart position shown in FIG. 2, as a result of which the clasp 2 is anchored in this medullary cavity. The anchoring is assisted by an undulating configuration preferably running in the plane of the arms.

Figure 3:
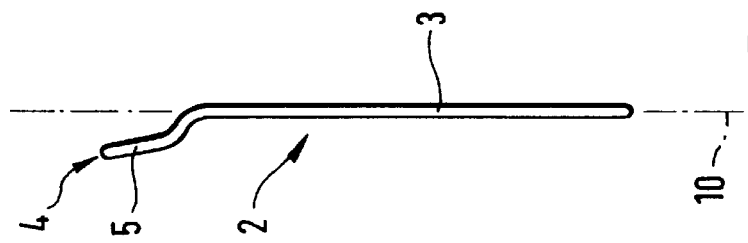
FIG. 3 shows the implant of the prior art in a side view.

As can be seen from FIGS. 1 and 3, the ends of the two arms delimiting the opening 6 and connected to each other at 4 are bent out from the plane 10 of the remaining part of the arms 3 and lie in a plane parallel to this plane 10 of the arms. This takes account of the lateral displacement of the two bone fragments 8, 9. The distance between these planes is adapted to this lateral displacement.

The clasp 2 in the prior art can consist of a flexurally elastic steel wire, in which case the distance between the two arms 3 in the unloaded state increases from the connection point 4 in the direction towards the free ends of the arms. The arms 3 are pressed together upon insertion into the medullary cavity, and they spread apart in the medullary cavity after the pressure exerted manually on the arms is ended.

Figure 5:
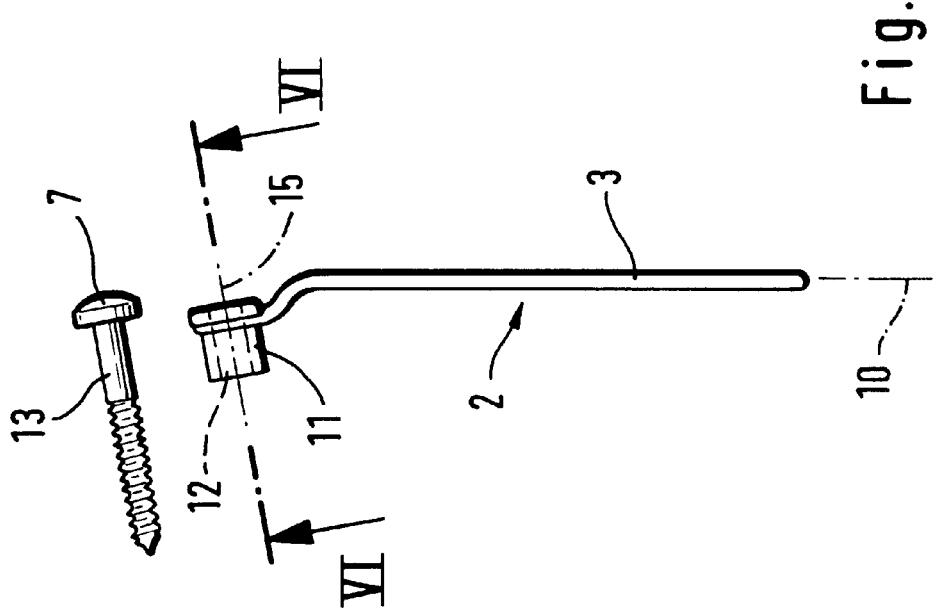
FIG. 5 shows the embodiment from FIG. 4 in a side view.
Figure 4:
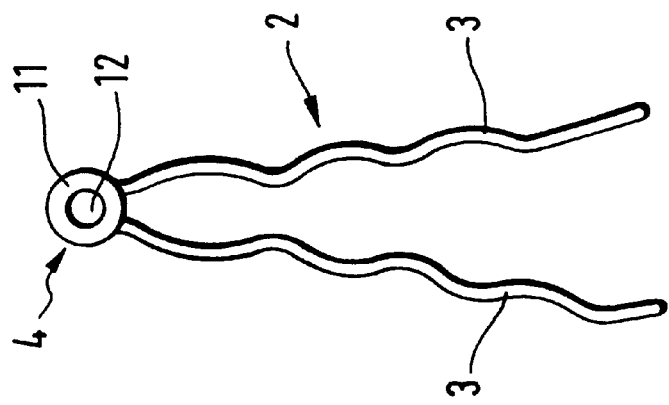
FIG. 4 shows an embodiment of the implant according to the invention in a plan view.

Although, in the implant of the prior art in FIGS. 1 to 3, the screw 7 in the implanted state presses the eyelet 5 against the bone fragment 8, a certain angle movement cannot be excluded upon loading of the bones, and this can obviously lead to serious problems. According to the invention, this can be avoided by the screw not just being held by the eyelet 5, but by a guide bushing 11 being inserted into the eyelet 5, as is shown in FIGS. 4 to 8. This guide bushing 11 has a cylindrical through-bore 12 which corresponds to the cylindrical part 13 near the head of the screw 7. In this way, it is possible to prevent an angle movement of the screw 7 in the guide bushing 11 and thus in relation to the clasp 2. As is shown in FIG. 5, the axis 15 of the bore 12 of the guide bushing 11 is arranged relative to the plane 10 of the arms at an angle other than 90° in order thereby to achieve better adaptation to the force resultant, in particular at an angle of approximately 75°.

Figure 6:
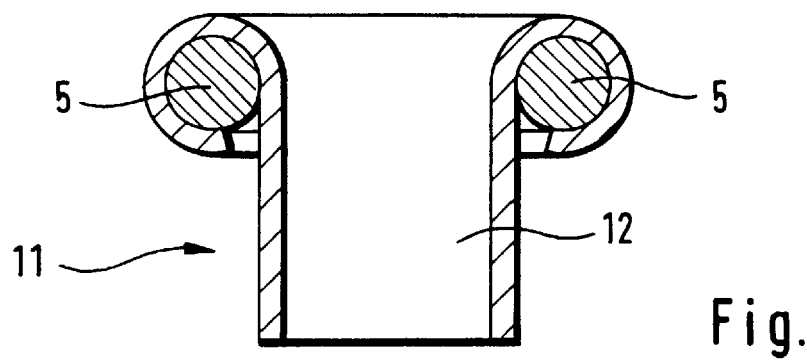
FIGS. 6 to 8 shows cross sections on the line VI—VI in FIG. 5 through various embodiments of the implant according to the invention.

As is shown in FIG. 6, the guide bushing 11 has an edge which is bent around the eyelet 5 so as to reliably secure the guide bushing 11. In the embodiment in FIG. 7, which corresponds roughly to the embodiment in FIG. 5, the guide bushing 11 has a greater external diameter and recesses 14 which partially receive the eyelet 5.

Figure 7:
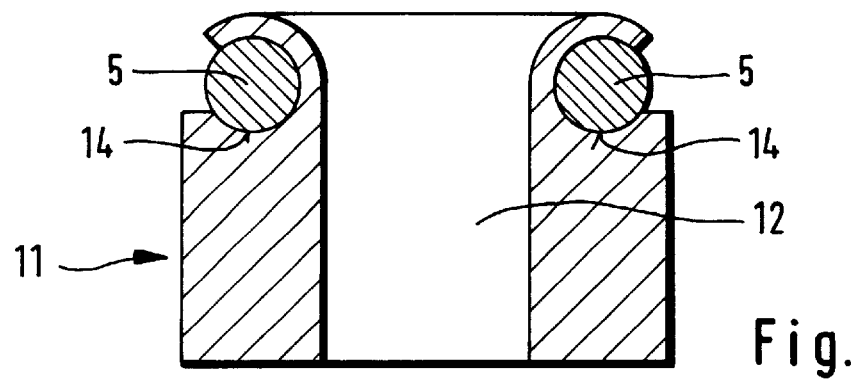
Figure 8:
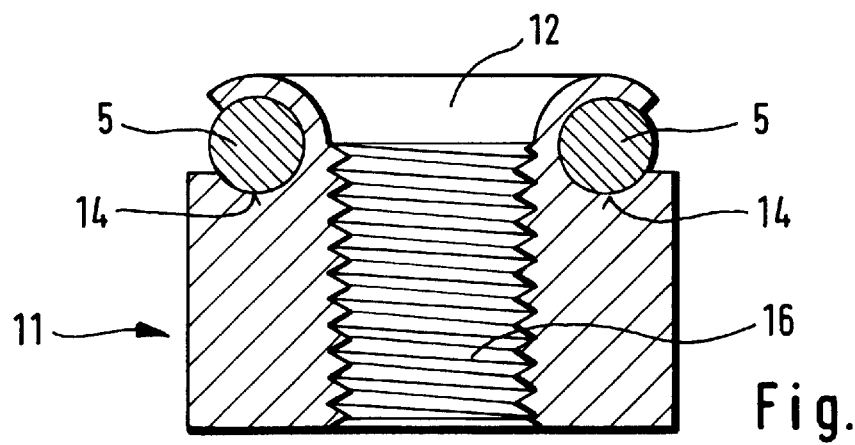

Whereas the bore 12 is substantially cylindrical in the embodiments in FIGS. 4 to 7, it is provided with a thread 15 in the embodiment in FIG. 8, which otherwise corresponds to the embodiment in FIG. 7, said thread 15 corresponding to the thread of the screw 7 which in this case however is not designed with the cylindrical part 13. Instead, the thread of the screw 7 in this case extends as far as the screw head.

The embodiment illustrated in FIG. 9 shows an embodiment of the invention where the axis 15 of the bore 12 of the guide bushing 11 is arranged relative to the plane 10 of the arms at an angle of approximately 90°. In this embodiment the portion of the arms 3 forming the clasp eyelet lie substantially in a plane which is parallel and offset in relation to the plane 10 of the arms 3.

What is claim is:

1. Implant for fixing two bone fragments to each other, in particular for fixing an axially corrected capitulum of a metatarsal bone, e.g. hallux valgus, which implant comprises a clasp with two arms which are connected to each other at one of their ends and in this area form an eyelet with an opening for passage of a screw which can be screwed into one of the two bone fragments, and which, with their other free ends, can be introduced into the other bone fragment, characterized in that it has a guide bushing for the screw, which guide bushing is inserted into the clasp eyelet and is secured thereon, its inner surface corresponding substantially to the outer surface of the screw in the area adjoining the screw head, and its minimum internal diameter being at least as great as the maximum diameter of the screw thread, the screw being held in the guide bushing substantially free of play.

2. Implant according to claim 1, characterized in that the inner surface of the guide bushing is substantially cylindrical.

3. Implant according to claim 2, characterized in that the guide bushing has an edge area engaging at least partially around the clasp eyelet.

4. Implant according to claim 3, characterized in that the guide bushing has an annular recess at least partially receiving of the clasp eyelet.

5. Implant according to claim 2, characterized in that the guide bushing has an annular recess at least partially receiving of the clasp eyelet.

6. Implant according to claim 2, characterized in that the ends of the arms forming the clasp eyelet lie substantially in a plane which is parallel and offset in relation to the plane of the arms in which the remaining part of the arms lies.

7. Implant according to claim 2, characterized in that the inner surface of the guide bushing has a length of at least 3 mm in the axial direction.

8. Implant according to claim 2, characterized in that the ads of the inner surface of the guide bushing forms, with the plane of the arms, an angle other than 90.

9. Implant according to claim 1, characterized in that the guide bushing has an edge area engaging at least partially around the clasp eyelet.

10. Implant according to claim 9, characterized in that the guide bushing has an annular recess at least partially receiving of the clasp eyelet.

11. Implant according to claim 9, characterized in that the ends of the arms forming the clasp eyelet lie substantially in a plane which is parallel and offset in relation to the plane of the arms in which the remaining part of the arms lies.

12. Implant according to claim 9, characterized in that the inner surface of the guide bushing has a length of at least 3 mm in the axial direction.

13. Implant according to claim 9, characterized in that the axis of the inner surface of the guide bushing forms, with the plane of the arms, an angle other than 90.

14. Implant according to claim 1, characterized in that the guide bushing has an annular recess at least partially receiving the clasp eyelet.

15. Implant according to claim 14, characterized in that the ends of the arms forming the clasp eyelet lie substantially in a plane which is parallel and offset in relation to the plane of the arms in which the remaining part of the arms lies.

16. Implant according to claim 14, characterized in that the inner surface of the guide bushing has a length of at least 3 mm in the axial direction.

17. Implant according to claim 1, characterized in that the ends of the arms forming the clasp eyelet lie substantially in a plane which is parallel and offset in relation to the plane of the arms in which the remaining part of the arms lies.

18. Implant according to claim 17, characterized in that the inner surface of the guide bushing has a length of at least 3 mm in the axial direction.

19. Implant according to claim 1, characterized in that the inner surface of the guide bushing has a length of at least 3 mm in the axial direction.

20. Implant according to claim 1, characterized in that the axis of the inner surface of the guide bushing forms, with the plane of the arms, an angle other than 90.

* * * * *

UNITED STATES PATENT AND TRADEMARK OFFICE
CERTIFICATE OF CORRECTION

PATENT NO. : 6,689,136 B2
DATED : February 10, 2004
INVENTOR(S) : Stoffella

It is certified that error appears in the above-identified patent and that said Letters Patent is hereby corrected as shown below:

Column 4,
Line 47, delete "ads" and insert therefor -- axis --.

Signed and Sealed this

Third Day of May, 2005

JON W. DUDAS
*Director of the United States Patent and Trademark Office*